United States Patent
Deban et al.

(10) Patent No.: US 6,389,305 B1
(45) Date of Patent: May 14, 2002

(54) METHOD AND APPARATUS FOR DETECTION OF CANCEROUS AND PRECANCEROUS CONDITIONS IN A BREAST

(75) Inventors: Abdou F. Deban, Sterling Heights, MI (US); David M. Tumey, San Antonio, TX (US); Kevin Buckman, Stockton, CA (US); Tony Xu, San Antonio, TX (US)

(73) Assignee: Lifeline Biotechnologies, Inc., Reno, NV (US)

( * ) Notice: Subject to any disclaimer, the term of this patent is extended or adjusted under 35 U.S.C. 154(b) by 0 days.

(21) Appl. No.: 09/294,735

(22) Filed: Apr. 19, 1999

Related U.S. Application Data (62) Division of application No. 08/884,307, filed on Jun. 27, 1997, now Pat. No. 5,941,832, which is a continuation-in-part of application No. 08/681,027, filed on Jul. 22, 1996, now abandoned, which is a continuation of application No. 08/168,081, filed on Dec. 15, 1993, now abandoned, which is a continuation of application No. 08/168,524, filed on Dec. 15, 1993, now abandoned.

(51) Int. Cl.7 .................................................. A61B 6/00
(52) U.S. Cl. ........................ 600/427; 600/408; 600/547
(58) Field of Search ................................ 600/427, 408, 600/547, 407, 474, 549; 382/128, 132; 378/37

(56) References Cited

U.S. PATENT DOCUMENTS

| | | | | |
|---|---|---|---|---|
| 5,301,681 A | * | 4/1994 | DeBan et al. | |
| 5,491,627 A | * | 2/1996 | Zhang et al. | |
| 5,673,332 A | * | 9/1997 | Nishikawa et al. | |
| 5,803,082 A | * | 9/1998 | Stapleton et al. | |
| 5,832,103 A | * | 11/1998 | Giger et al. | 382/130 |
| 5,941,832 A | * | 8/1999 | Tumey et al. | |
| 5,987,094 A | * | 11/1999 | Clarke et al. | |
| 6,058,322 A | * | 5/2000 | Nishikawa et al. | |
| 6,067,371 A | * | 5/2000 | Gouge et al. | |
| 6,088,473 A | * | 7/2000 | Xu et al. | |

* cited by examiner

Primary Examiner—Marvin M. Lateef
Assistant Examiner—Shawna J Shaw
(74) Attorney, Agent, or Firm—R. William Graham (57) ABSTRACT

An apparatus for detection of precancerous and cancerous conditions in a breast is provided and includes a computer for digitizing at least one of a mammogram image data and a (scinti)mammogram image data of a breast, computer-based software operably associated with the computer based means for manipulating at least one of said digitized mammogram image data and said digitized (scinti)mammogram image data and generating at least one of a mammogram ROI image and a (scinti)mammogram ROI image data indicative of precancerous and cancerous condition, and monitor operably associated with the computer based means for concurrently visually displaying at least one of said digitized mammogram image data and said digitized (scinti) mammogram image data and said mammogram ROI image and said (scinti)mammogram ROI image data in a superimposed manner.

24 Claims, 5 Drawing Sheets

METHOD AND APPARATUS FOR DETECTION OF CANCEROUS AND PRECANCEROUS CONDITIONS IN A BREAST

| 09294735 | DIV | 08884307 | 5941832 | PATENTED | 06/27/1997 |
|----------|-----|----------|---------|----------|------------|
| 08884307 | CIP | 08681027 |         | ABANDONED | 07/22/1996 |
| 08681027 | CON | 08168081 |         | ABANDONED | 12/15/1993 |
| 08168081 | CON | 08168524 |         | ABANDONED | 12/15/1993 |

BACKGROUND OF THE INVENTION

This invention is directed to a method and apparatus for detection of an abnormal condition in breasts, and more particularly to, but not by way of limitation, a method and apparatus for detection of cancerous and precancerous conditions in breasts, as well as established normal breast conditions.

Presently, there exist several techniques for detecting breast cancer. These techniques attempt to provide a physician with information based on either anatomical or physiological anomalies to enable the physician to make a determination as to the condition of the breast and both of these are limited.

Radiologists fail to detect cancer in up to thirty percent of patients with breast cancer. Also, the malignancies missed by the radiologists are evident in two thirds of the mammograms. There is a need to further assist radiologists, surgeons and other physicians in detecting, diagnosing, successfully biopsying and operating on precancerous and cancerous conditions.

It is known that areas of mammalian tissue adjacent to carcinomas exhibit increased temperature from that exhibited contemporaneously by non-adjacent, non-cancerous areas. The temperature of the cancer-affected areas can fluctuate several degrees Centigrade from normal tissue; these differences having been demonstrated while monitoring such areas for a 24-hour period (one circadian cycle).

It had been thought that an abnormal temperature pattern associated with a tumor is a product of accelerated metabolism and numerous other factors, such as vaso-active substances and hormonal changes. Evidence now suggests that local metabolic heat generation may be a second order effect since the majority of thermal signals are related to the function of increased regional blood flow caused by local angiogenesis. A slight overall increase in the temperature of the surrounding tissue, for instance in localized areas of a woman's breast, can occur and is usually related to the vascular convection of heat that occurs as a result of capillary dilatation and the secondary increase in blood flow coupled with the higher temperature of the blood derived from the vascular bed and the possible vasodilator effect of catabolic products of a tumor metabolism. These vascular manifestations of heat production or cooling are of prime importance in the detection of subclinical or minimal cancers.

In addition, it is also known that tissue surrounding malignant lesions of the breast often contain groups of microcalcifications with discernible morphology and structure which can be detected and utilized in detecting breast cancers.

One prior device used for detecting cancer is a brassiere which includes a plurality of temperature sensors, an analog multiplexer circuit, a control circuit, a sample and hold circuit, an analog/digital converter, a buffer register, a storage register, a clock and a data logger. The device allows for the storage of temperature readings in a digital form. This digital data may be uploaded to the data logger which converts the digital signals to decimal form so that the temperature differences may be read and analyzed by a supervising physician.

Several problems exist with the brassiere device. The brassieres must be capable of fitting a full range of breast sizes since tissue contact is essential to provide acceptable device performance. Also, this system would be expensive requiring individual brassieres to be prepared for each user since it is unlikely that an individual would wear a brassiere which was previously worn by another person for extended periods of time due to the nature of the device. Thus, a disposable brassiere would be desired.

Furthermore, the temperature sensors of the brassiere device are affixed on its inner surface. Ideally, all sensors are in contact with the skin when the brassiere is positioned about the breast. Realistically, however, in the normal course of wear, the sensors will frequently not be in contact with the skin. Lack of contact causes the sensors to produce false skin temperature readings. It is also noted that such device does not disclose a need or means for calibrating the sensors. Any diagnosis based on uncalibrated sensor readings could be faulty.

Devices which use a passive thermographic analytical apparatus provide a direct readout of the results through analysis of a thermographic radiation pattern of the human body. Such devices include a matrix of infrared energy sensors and reflectors which are mounted in a closed, spaced array to produce a pattern of temperature measurements of the aligned areas of the body. The sensors simultaneously or sequentially read a thermographic pattern and develop analog signals which are converted into the appropriate digital form and are stored in a memory. The digital signals are then analyzed by a central processing unit (CPU) in accordance with a particular spatial pattern recognition software program. The program includes an algorithm having a number of parameters used in comparing differences in temperatures throughout the breasts to give a probability of breast normality or abnormality.

Unfortunately, such devices are unable to detect small tumors on the order of less than 0.5 cm and possibly other larger tumors as well, especially certain types of cancers. This seems to be due to the resolution and sensitivity capabilities of the thermographic sensors. Another problem with such devices is that the CPU will give inaccurate results if internal failure occurs at any point in the computer's probability program. Faulty readings from the thermographic pattern cause the software program to generate inaccurate results.

Of even greater concern, such thermographic devices do not take into account the chaotic fluctuation of normal body temperatures over time and between locations on the body. The temperatures between the left and right breasts may vary as much as 4 degrees Centigrade during anyone circadian cycle, as well as constant fluctuation throughout any 24-hour period. Since the patient is required to remain in front of the scanning apparatus of the thermographic device for only a short period of time in order to take a thermographic picture, which picture only represents one moment in time and is not representative of the actual condition of the breast over a long period of time. An analysis based on such thermographic results could be totally inaccurate.

As previously mentioned, one common and widely used technique for determining existence of breast cancer is mammography. This radiological technique passes ionizing radiation through the breast, which is per se invasive, to produce a radiograph which should report tumors as darkened areas. This method of detecting breast cancer is limited by the age of the patient and condition of the tissue examined. In addition, about sixty-six percent of cancer is missed by the radiologists in retrospect. Most cancer is diagnosed too late and successful diagnosis and treatment are more attainable if the cancer is found at early stages. If the tissue is dense, as is characteristic of breast tissue in younger women, the image produced is more uniform in gray scale causing detection of tumors to be more difficult.

In cases of breast implants, thirty percent of the breast may be undiagnosable. This is due to the visual and mammographic impairment in many cases.

Even though such prior devices have been somewhat effective, there remains a need to improve the method and device for detection of potentially cancerous conditions in breasts.

SUMMARY OF THE INVENTION

It is an object of the present invention to provide an improved method and device for detecting cancer.

It is yet another object of the present invention to provide a method and a device for an identification of regions of interest (ROI) in mammograms and (scinti)mammograms for detecting cancerous and precancerous conditions.

Another object is to assist physicians in doing surgery and biopsies on the breast.

The present invention is directed to a method and apparatus for detection of cancerous and precancerous conditions in breasts. The apparatus comprises computer-based means for digitizing a mammogram or (scinti)mammogram of a breast, first means operably associated with the computer-based means for manipulating the digitized mammogram image data and/or digitized (scinti)mammogram image data to generate mammographic ROI image data and/or (scinti) mammographic image ROI data, and means operably associated with the computer-based means for concurrently displaying the digitized mammogram image data and/or digitized (scinti)mammogram image data and the mammographic ROI image data and/or (scinti)mammographic ROI data.

The digitizing means includes a scanner operably connected to a CPU. The first manipulating means includes means for filtering, segmenting, and regionalizing the digitized (scinti)mammogram image to produce the ROI data. The first manipulating means further includes a neural network.

The invention further includes means for sensing at least one of breast temperatures and electro-physiological data and generating signals in response thereto, second means operatively associated with the sensing means for receiving and manipulating the signals for generating at least one of therm-physiological data and electro-physiological data indicative of precancerous and cancerous conditions in the breast and wherein the display means concurrently displays the digitized mammogram image data and/or digitized (scinti)mammogram image data, the mammographic ROI image data and/or (scinti)mammographic ROI image data and at least one of the thermo-physiological data and electro-physiological data in a superimposed manner. The displaying means further includes means for associating a unique visual attribute for at least one of the digitized mammogram image data, digitized (scinti)mammogram image data, the mammographic ROI image data, the (scinti) mammographic ROI image data, the thermo-physiological ROI data and the electro-physiological ROI data.

The receiving and manipulating means includes processing means having non-algorithmic logic which utilizes prior pathological data in correspondence with the sensed signals to manipulate the signals and produce the thermo-physiological data and the electro-physiological is data.

The manipulating means may further include a neural network having predetermined solution space memory, the solution space memory including regions indicative of cancerous and non-cancerous conditions, wherein the thermo-physiological data and the electro-physiological data produces the signals being projected into said regions.

The device further includes means operatively connecting the sensing means and the receiving and manipulating means, the connecting means includes means for receiving and storing the signals from the sensing means, means for controlling transmission of the signals from the sensing means to the storing means, and means for calibrating the sensing means for use in generating the thermo-physiological data.

Also, provided is a method for determining cancerous conditions in a breast. The method comprises the steps of (a) digitizing a mammogram or (scinti)mammogram, (b) manipulating the digitized data to produce mammographic ROI image data and/or (scinti)mammographic ROI image data indicative of precancerous and cancerous conditions in the breast, (c) digitizing at least one of thermo-physiological data signals and electro-physiological data signals taken from the breast into at least one of the thermo-physiological digitized data and the electro-physiological digitized data (d) manipulating the at least one of the thermo-physiological digitized data and the electro-physiological digitized data for generating at least one of a thermo-physiological ROI data and an electro-physiological ROI data about the signals indicative of precancerous and cancerous conditions in the breast and (e) concurrently displaying the mammographic ROI image data and/or (scinti)mammographic ROI image data and at least one of the thermo-physiological ROI data and the electro-physiological ROI data on a suitable display monitor such as a high resolution CRT.

The present invention is more particularly described in the drawings and specification which follow. Other objects and advantages will be more readily apparent upon reading the following.

DETAILED DESCRIPTION OF THE PREFERRED EMBODIMENT

Figure 6:
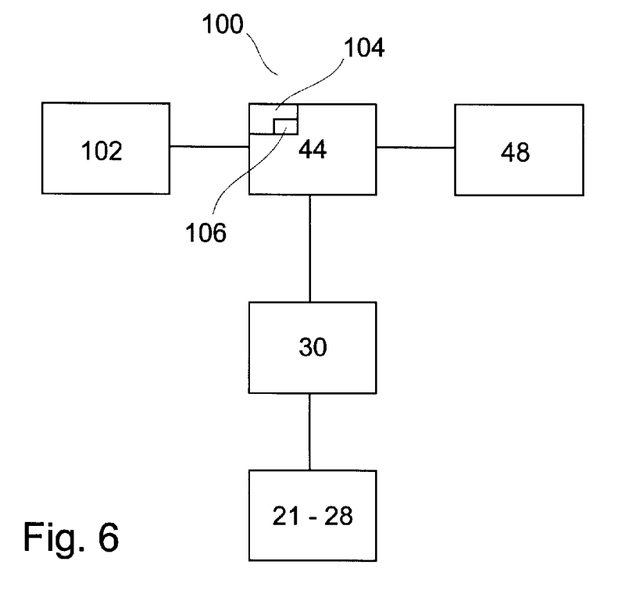
FIG. 6 discloses a schematic of the device of the present invention.
Figure 7:
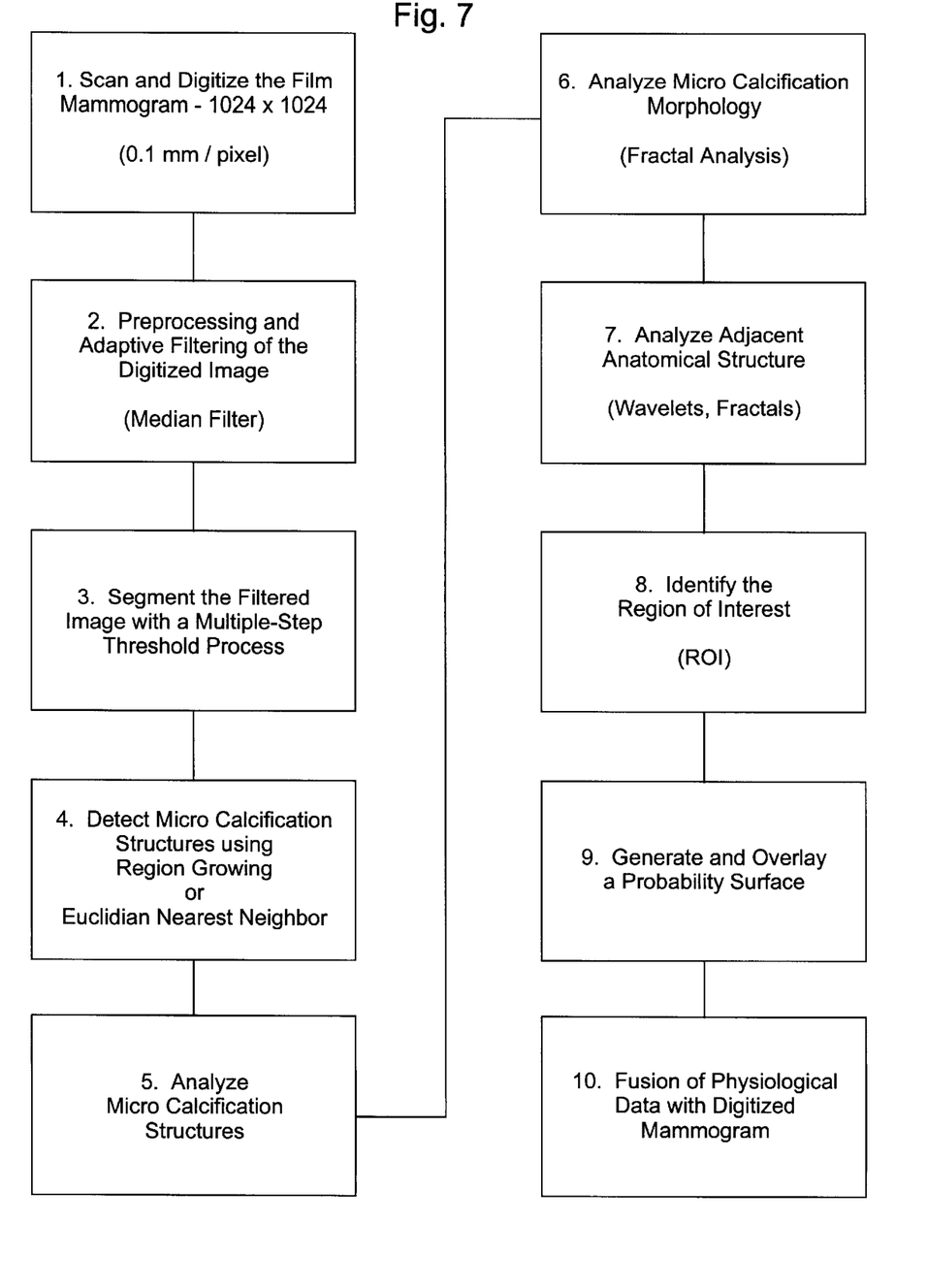
FIG. 7 shows a block diagram of the steps performed by the method of the present invention.

FIG. 6 generally depicts the apparatus of the present invention and is generally represented by the numeral 100. The apparatus 100 generally includes a CPU 44, a scanning device 102 operably connected to the CPU 44, a display 48 operably connected to the CPU 44 and harness 30 with its electro physiological/thermo-physiological sensors 21–28 as more filly set forth herein below.

The scanning device 102 should be of a type which scans at a rate for digitization, preferably of about 0.1 mm per pixel. An Imagitex model 1085 (Nashua, N.H.) has been found suitable which is capable of 1024×1024 pixel optimal resolution. Each pixel can be assigned one of 255 intensity levels (8 bits). Higher bit resolution, such as 10 or 12, may be desirable. With the stated scan rate, resolution of calcifications as small as 0.1×0.1 mm is readily attainable.

The CPU 44 has a memory 104 for storing a digitized mammogram image data or digitized (scinti)mammogram image data produced via scanning a mammogram image data or a (scinti)mammogram image data using the scanning device 102. The memory 104 also includes a filtering device 106, preferably resident on the memory 104 in the form of software. The filtering device 106 includes non-linear filtering software, such as conventional median filtering, to reduce noise in the digitization of mammogram image data or (scinti)mammogram image data. Median filtering, which utilizes the median value of a neighborhood of pixels, is employed as an area process utilizing either a box or cross kernel ascertainable to a person skilled in the art, and is useful in minimizing line displacement and preserving sharpness of edges, lines and corners. These surface structures are required for an effective analysis of microcalcification morphology. Pixel intensity changes are efficiently detected using a two dimensional difference of Gaussian or Laplacian of Gaussian filter kernel, based on the anticipated detection size of the target microcalcification. Here, the Gaussian techniques destroy any unwanted spatial resolution that fall outside the parameters of the Gaussian filter. The Difference or Laplacian operator can then detect intensity changes more readily from the remaining digitized mammogram image data and/or the digitized (scinti) mammogram image data.

The filtering device 106 also includes a segmenting software, utilizing adaptive thresholding, wherein each scanned pixel of the digitization mammogram image data and/or (scinti)mammogram image data is evaluated to see whether it meets a predetermined intensity threshold. Each pixel is further evaluated to determine whether the pixel is within an acceptable intensity offset to the surrounding tissue. The "offset" is the average intensity of pixels surrounding, but excluding the identified pixel in a predetermined pixel neighborhood. The average intensity is subtracted from the individual pixel intensity and the difference compared to a predetermined threshold range. A ratio test is applied to determine if the intensity ratio of the pixel to the average value in the immediate surrounding area meets a minimum threshold. If each of the criteria is met, the pixel is associated as being part of a calcification.

Each pixel associated as being part of a calcification is identified and grouped (in clusters with adjacent pixels) as microcalcifications. A maximum dimension for each microcalcification, the surrounding tissue and other suspicious areas and lesions are determined and compared to an allowable microcalcification size defined by a predetermined maximum and minimum range.

Intensity gradients are also computed for each pixel and its surrounding pixels in the cluster and outside the cluster. The gradient is computed and compared with predetermined mean and variance criteria. The minimal distance center of the calcification pixel cluster is then identified as well as measurements of tissue around microcalcifications and its morphology.

Regions of clusters can be defined by sets of pixels in separate matrices, wherein each matrix may include one or more pixel. If the number of detected microcalcifications exceeds a predetermined threshold per unit volume (e.g., 3 microcalcifications in a 1 cm cubic volume), a cluster of microcalcifications is identified. A pixel-inclusion operation is implemented which is governed by a dynamic test for inclusion based on the average intensity value and variance of pixels contained in the connected cluster, wherein each pixel can only be a member of one matrix.

Clusters are then analyzed using certain rules (i.e., neural network logic as described herein below). Clusters which are found to meet certain predetermined criteria are marked as "clinically significant" and noted by the degree of suspicion by color or graphic coding to denote the degree or amount of likelihood of probability of breast disease.

Clinically significant microcalcifications are then determined to be either benign or malignant. This determination is made with the aid of a further software filter, such as fractal-based algorithm or a neural network of a similar type described below, which looks at the microcalcification morphology. In addition to morphology, the average pixel intensity, region ratio averages, offset region averages and microcalcification sizes and dimension ratios can all be utilized in generating mammogram ROI image data and/or (scinti)mammographic ROI image data.

Figure 8:
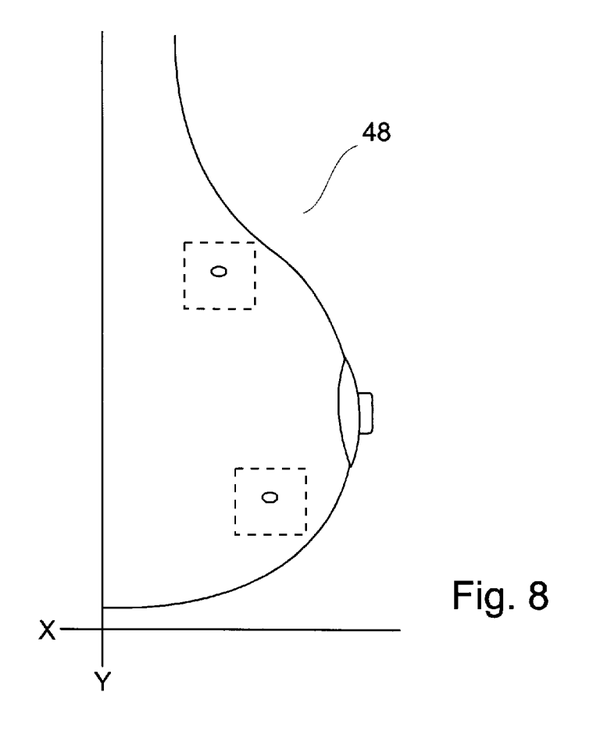
FIG. 8 shows a display depicting mammographic image data and/or (scinti)mammographic image data and one of the mammographic ROI image data, the (scinti)mammographic ROI image data, the thermo-physiological ROI data and electro-physiological ROI data in a superimposed manner.

Fractal analysis as well as wavelet analysis of the above factors provides a window data of the image immediately surrounding the microcalcification clusters and helps the radiologist in evaluating the mammographic ROI image data and/or (scinti)mammographic ROI image data. The display monitor 48 is utilized here to display the mammographic image data and/or (scinti)mammographic image data with a superimposed ROI image data as seen in FIG. 8. The CPU 44 associates a unique visual attribute for display by the display monitor 48 with each of the mammographic image data and/or (scinti)mammogram image data and the mammographic ROI image data and/or (scinti)mammographic ROI image data to aid in distinguishing the same. Particularly, a window is associated with mammographic ROI image data and/or (scinti)mammographic ROI image data signal and displayed as pseudo-colors superimposed over the mammographic image data and/or (scinti) mammographic image (e.g., in a gray scale, for example) which indicate probability of malignancy.

Figure 1:
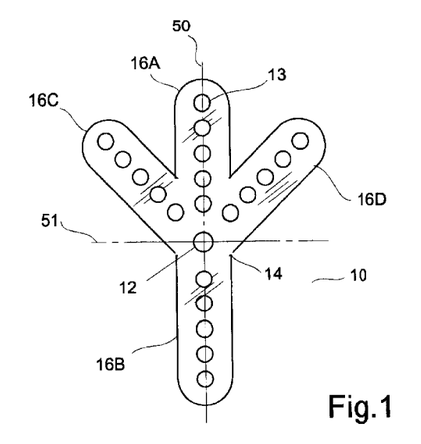
FIG. 1 shows the template of the present invention.

FIG. 1 illustrates template 10. The template 10 is made of a material capable of conforming to a mammalian breast and surrounding breast tissue on the chest wall area. When the template is properly oriented, the template 10 has a plurality of openings 12 and 13 which are spatially positioned in accordance with areas of the breast pathologically determined to be highly susceptible to cancer development. As shown in FIG. 1, the template 10 has a center portion 14 and four arms 16*a–d* extending radially outward from central portion 14. The template 10 is of a sufficient size to accommodate numerous breast sizes. Central portion 14 has the opening 12 centrally defined therein which is placed over the breast nipple to position the template. Each arm 16a–d has a sufficient quantity of the openings 13 to accommodate differing breast sizes such that at least one opening per arm can be placed over a breast area desired to be sensed.

Areas of the breast to be sensed, for example, are those where cancer development is most likely to occur, can be marked by orienting the template 10 on a breast as shown in FIG. 1. Arms 16a and 16b extend along the vertical midline 50 of the breast with arm 16a above and arm 16b below the horizontal midline 51 of the breast. Arms 16c and 16d extend diagonally to bisect the upper outer quadrant and upper inner quadrant of the breast, respectively. On the patient's other breast, the position of arms 16c and 16d are reversed which allows for symmetrical markings of the breasts, important in obtaining an accurate diagnosis.

Figure 2:
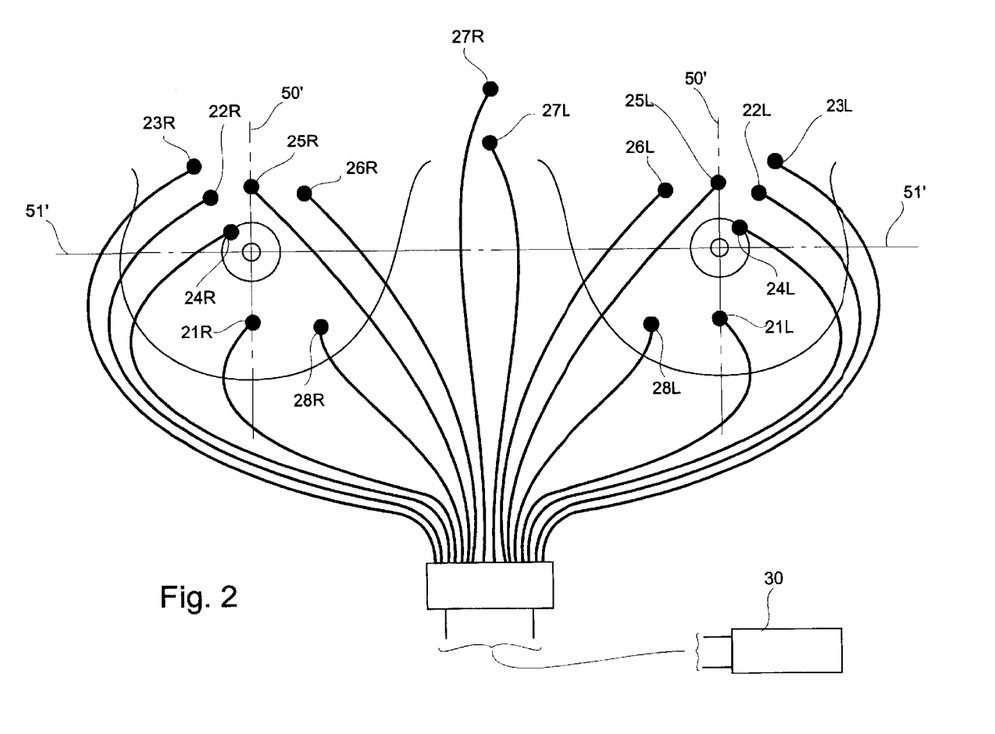
FIG. 2 shows the sensors and harness block of the present invention.

Once location of desired sensor placement has been determined, the sensors 21–28 (in the preferred embodiment the sensors are thermistors) are affixed to the breast tissue. FIG. 2 illustrates electro-physiological/thermo-physiological sensors (thermistors) 21L–28L and 21R–28R positioned on the breasts and attached to harness block 30 according to the invention. Thermistors 21L–28L and 21R–28R are positioned over the marked areas of the right and left breasts which have been determined by use of template 10. Specifically, thermistors 21L–28L and 21R–28R are placed on the breasts as follows: 21L and 21R below the nipple; 22L and 22R in the upper outer quadrant; 23L and 23R in the upper outer quadrant toward the axilla; 24L and 24 R on the upper areola; 25L and 25R on vertical midline 50' above horizontal midline 51'; 26L and 26R in the upper inner quadrant; 27L in an ambient temperature zone; 27R on the sternum; 28L and 28R on other areas of concern and at contralateral positions. Each pair of the thermistors (e.g., 21L/21R, 22L/22R, etc.) is preferably marked to allow for easy identification of each thermistor pair as well as each thermistor. For example, each thermistor pair is color coded and tabbed with a number and letter.

Each thermistor and its signals are consequently identified with a specific position on the breast. This consistency simplifies subsequent processing and improves accuracy of the signals in terms of individual signal correlation with calibration data and selection of specific signal sources for manipulation in developing the generalization of physiological condition. This also simplifies correlation of results with specific sensor positions on the breast to arrive at a more specific determination of the location of abnormal physiological condition. While the number of thermistors and positioning are specifically set forth, it is conceived that accuracy increases as the number of thermistors increases.

Each of the thermistors 21L–28L and 21R–28R is made of an electrically conductive material (e.g. nickel-manganese oxide). Each thermistor produces a resistance which varies with the temperature measured. With respect to obtaining thermo-physiological data, an important feature resides in the calibration system of the thermistors 21–28. In the present invention, the Steinhart and Hart equation, an empirical expression, has been determined to be a suitably desirable signal transform algorithm for the resistance—temperature relationship. It is usually found explicit in T, with:

$$1/T = a + b(Ln\ R) + C(Ln\ R)3$$

and in which T is the Kelvin temperature, Ln is the Logarithm of R to the base e and a, b and c are coefficients derived from measurement.

Normalization coefficients a, b and c are found by making measurements of R at three Temperatures (20 degrees, 30 degrees, and 40 degrees C.) and solving simultaneously:

$$1T/= a + b(Ln\ R1) + C(Ln\ R1)3$$

$$1/T2 = a + b(Ln\ R2) + C(Ln\ R2)3$$

$$1/T3 = a + b(Ln\ R3) + C(Ln\ R3)3.$$

Over a temperature range of 20 degrees to 40 degrees Centigrade (C.), this algorithm produces an accurate fit. Because each thermistor has slightly different physical and chemical properties, the resistance of each thermistor is measured at 20 degrees C., 30 degrees C., and 40 degrees C. in a stirred nonconductive fluid bath, (e.g. BLANDOL™ available from Sealand Chemical, Silicon oil or FLURINERT 40™ available from Sealand Chemical), the fluid temperature measured by a NIST standard thermometer, and the specific normalization coefficients for each thermistor determined by inserting the resistance of each thermistor at each temperature into and simultaneously solving the foregoing equations.

Figure 3:
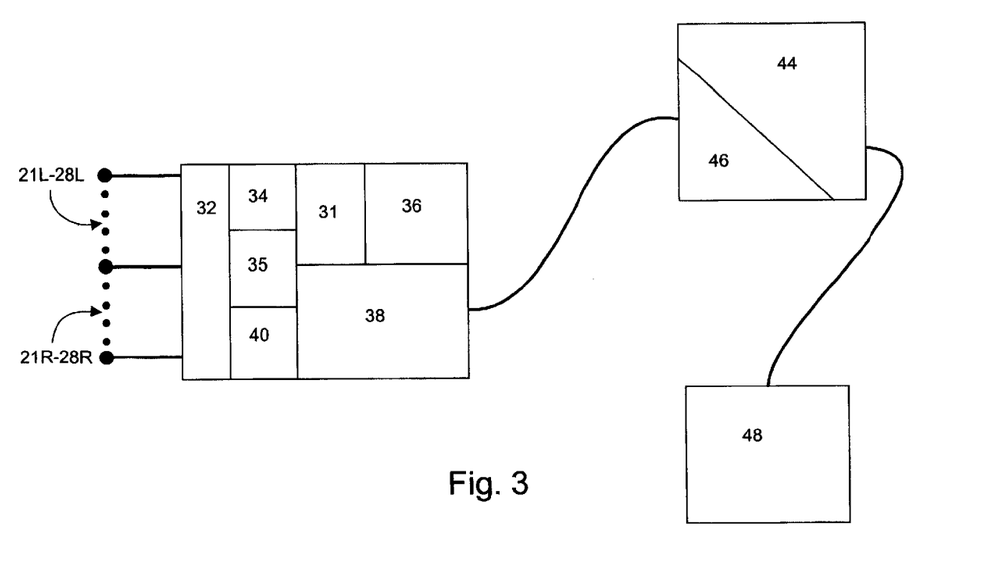
FIG. 3 is a schematic drawing of a part of the present invention.

Referring to FIG. 3, these coefficients are referred to as calibration data which are stored in memory 31 (read only memory, for example) of harness 30 and identified as relating to a specific thermistor. An important aspect of the present invention is that the calibration data is stored in harness block 30. In the field of use, many harness blocks will exist. Accessing each thermistor's calibration data contemporaneously with its respective stored signals from the harness block will remove the potential for processing errors occurring from mismatching calibration data and thermistors.

Each of thermistors 21L–28L and 21R–28R is connected to an analog multiplexer 32 which allows for simultaneous transmission of signals from the thermistors 21L–28L and 21R–28R to analog/digital (A/D) converter 34. Each signal is then amplified by amplifier 35 and applied to A/D converter 34 which converts each analog signal into a suitable multiple bit binary number or digital word suitable for processing.

Within harness 30, an oscillator type system clock 40 supplies pulses to CPU 38. Upon receiving a predetermined number of pulses, CPU 38 initiates multiplexer 32 to poll thermistors 21L–28L and 21R–28R by gating signals from each thermistor 21L–28L, 21R–28R. CPU 38 controls the transmission and storing of the signals in random access memory 36. Multiplexer 32, A/D converter 34, memory 36, CPU 38, clock 40, and amplifier 35 are of any suitable construction as is known in the art.

FIG. 3 shows the CPU 44 operatively associated with neural network 46 and CPU 38. CPU 44 is capable of uploading data from memory 31 and 36 and channeling the data through neural network 46. The CPU 44 can be a commercially available microprocessor which uses the software system described herein below. Alternatively, a commercially available microprocessor can be integrated with a commercially available neurocomputer accelerator board, such as the one available from Science Applications International Corp. (SAIC).

Neural network 46 utilizes parallel processing which allows quantities of information, or data, to be analyzed more quickly and in a different fashion than is permitted in serial processing. Generally speaking, neural network paradigms make no assumptions about the data and feature extraction is automatically performed. The network itself selects, through a non-algorithmic process, features of the input data on which it focuses at any point during data processing and manipulation. Where the desire is to receive output results related to normal or abnormal physiological condition, the features are weighted based on pathological evidence and other empirical data introduced into the neural network through what is referred to as a training process.

The neural network training process entails the creation of a solution space memory. Solution space memory as used herein refers to multidimensional space created internal to the neural network containing regions associated with pathological determinations of non-cancerous normal physiological condition and other regions associated with cancerous abnormal physiological conditions. The training process further entails iteratively entering empirical data, risk factors, imaging data and pathological evidence and modulating the neural network based upon its output. This iterative training accomplishes several purposes, first refining the definition of the regions associated with each condition in the solution space memory, and second causing the neural network to determine the non-algorithmic process by which it projects new data signals into the solution space. Following training, the neural network, will manipulate and project input signals into the solution space memory and the resulting intersection of those signals with one or more solution space regions produces a generalization about the signal indicative of cancerous abnormal or non-cancerous normal physiological condition. Provided that sufficient pathological and other empirical data is available to train the neural network, its manipulation methodology, based on parallel processing, produces results consistent with non-invasive and invasive pathological determinations made through mammography, biopsy techniques and surgical techniques. The display 48 is connected to the CPU 44 such that the display 48 provides visual display of the results generated by the neural network 46 and CPU 44 based upon the input data received.

Figure 4:
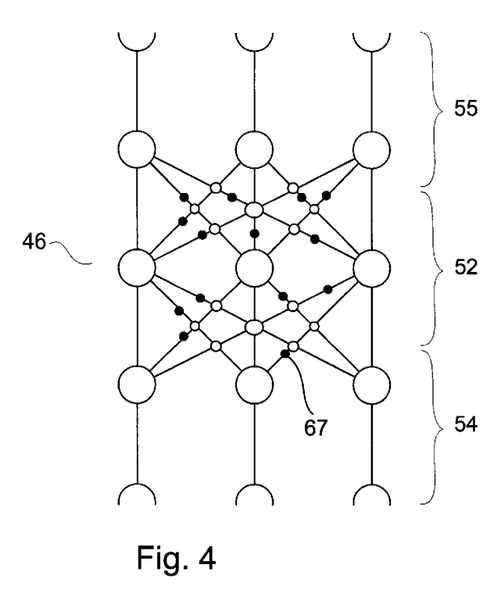
FIG. 4 is a general diagram of the neural network of the present invention.

As shown in FIG. 4, the neural network 46 includes at least one layer of trained neuron-like units, and preferably at least three layers. The neural network 46 includes input layer 55, hidden layer 52, and output layer 54. Each of the input, hidden, and output layers include a plurality of trained neuron-like units.

The neuron-like units of the input layer include a receiving channel for receiving a sensed signal, wherein the receiving channel includes a predetermined modulator for modulating the signal. The neuron-like units of the hidden layer are individually receptively connected to each of the units of the input layer. Each connection 67 includes a predetermined modulator for modulating each connection between the input layer and the hidden layer.

The neuron-like units of the output layer are individually receptively connected to each of the units of the hidden layer. Each connection 67 includes a predetermined modulator for modulating each connection between the hidden layer and the output layer. Each unit of said output layer includes an outgoing channel for transmitting the modulated signal.

Figure 5:
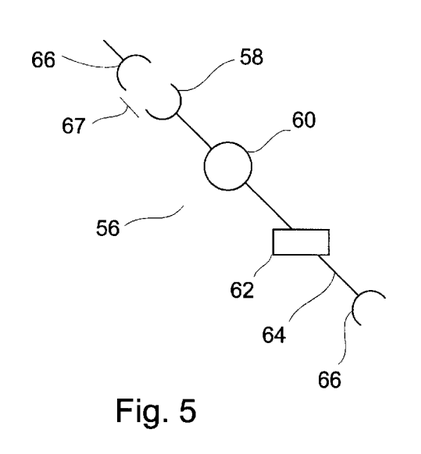
FIG. 5 represents a neuron-like unit of the present invention.

Referring to FIG. 5, each trained neuron-like unit 56 includes a dendrite-like unit 58, and preferably several, for receiving digitized incoming signals. Each dendrite-like unit 58 includes a particular modulator 60 which modulates the amount of weight which is to be given to the characteristic sensed by modulating the incoming signal and subsequently transmitting a modified signal. For software, the dendrite-like unit 58 includes an input variable $X_a$ and a weight value $W_a$ wherein the connection strength is modified by multiplying the variables together. For hardware, the dendrite-like unit 58 can be a wire, optical or electrical transducer having a chemically, optically or electrically modified resistor therein.

Each neuron-like unit 56 includes soma-like unit 62 which has a threshold barrier defined therein for the particular characteristic sensed. When the soma-like unit 62 receives the modified signal, this signal must overcome the threshold barrier whereupon a resulting signal is formed. For software, the soma-like unit 62 is represented by the sum $S=(\Sigma_a X_a * W_a)-\beta$, where $\beta$ is the threshold barrier. This sum is employed in a Nonlinear Transfer Function (NTF) as defined below. For hardware, the soma-like unit 62 includes a wire having a resistor; the wires terminating in a common point which feeds into an operational amplifier having a nonlinear part which can be a semiconductor, diode, or transistor.

The neuron-like unit 56 includes an axon-like unit 64 through which the output signal travels, and also includes at least one bouton-like unit 66, and preferably several, which receive the output signal from axon-like unit 64. Bouton/dendrite linkages form the connection 67 from the input layer to the hidden layer and from the hidden layer to the output layer. For software, the axon-like unit 64 is a variable which is set equal to the value obtained through the NTF and the bouton-like unit 66 is a function which assigns such value to a dendrite-like unit of the adjacent layer. For hardware, the axon-like unit 64 and bouton-like unit 66 can be a wire, an optical or electrical transmitter.

The modulators of the input layer modulate the amount of weight to be given various physiological characteristics such as, but not necessarily limited to, temperature, temperature fluctuation, area of the body sensed, physiological period of month (menstrual), and pre or perimenopausal status, morphology, size, intensity and number of the tissue calcifications.

For example, if a patient's tissue temperature is higher than, lower than, or in accordance with what has been predetermined as normal, the soma-like unit would account for this in its output signal and this bears directly on the neural network's decision to indicate whether a normal non-cancerous or an abnormal precancerous or cancerous condition exists.

The modulators of the output layer modulate the amount of weight to be given for indicating normal non-cancerous physiological conditions or abnormal precancerous or cancerous physiological conditions. It is also possible, however, to assign weighting unit values to output neuron-like units which represent a probability of normal or abnormal conditions, e.g. 90 percent likely to be abnormal cancerous conditions. It is not exactly understood what weight is to be given to characteristics which are modified by the modulators of the hidden layer, as these modulators are derived through a training process defined below.

The training process is the initial process which the neural network must undergo in order to obtain and assign appropriate weight values for each modulator. Initially, the modulators and the threshold barrier are assigned small random non-zero values. The modulators can be assigned the same value but the neural network's learning rate is best maximized if random values are chosen. Pathological and other empirical data taken from control group subjects over one period up to forty-eight hours at predetermined intervals is input in parallel into the dendrite-like units of the input layer and the output observed.

The NTF employs S in the following equation to arrive at the output:

$$NTF = \frac{1}{[1 + e^{-S}]}$$

For example, in order to determine the weight to be given to each modulator for the particular physiological variable, the NTF is employed as follows:

If the NTF approaches 1, the soma-like unit produces an output signal indicating an abnormal condition. If the NTF approaches 0, the soma-like unit produces an output signal indicating a normal condition. If the output signal clearly conflicts with the known condition, pathologically determined, an error occurs. The weight values of each modulator are then adjusted using the following formulas so that the input data produces the desired empirical output signal.

For the output layer:

$$W^*_{kol} = W_{kol} + GE_k Z_{kos}$$

$W^*_{kol}$=new weight value for neuron-like unit k of the output layer.

$W_{kol}$=actual weight value obtained for neuron-like unit k of the output layer.

G=gain factor (usually less than 1.0)

$Z_{kos}$=current output signal of neuron-like unit k of output layer.

$D_{kos}$=desired output signal of neuron-like unit k of output layer.

$E_k = Z_{kos}(1-Z_{kos})(D_{kos}-Z_{kos})$, (this is an error term corresponding to neuron-like unit k of output layer).

For the hidden layer:

$$W^*_{jhl} = W_{jhl} + GE_j Y_{jos}$$

$W^*_{jhl}$=current weight value obtained for neuron-like unit j of the hidden layer.

$W_{jhl}$=current weight value obtained for neuron-like unit j of the hidden layer.

G=gain factor (generally less than 1)

$Y_{jos}$=actual output signal of neuron-like unit j of hidden layer.

$E_j = Y_{jos}(1-Y_{jos}) \Sigma_k E_k W_{kol}$, (this is an error term corresponding to neuron-like unit j of hidden layer over all k units).

For the input layer:

$$W^*_{iil} = W_{iil} + GE_i X_{ios}$$

$W^*_{iil}$=new weight value for neuron-like unit i of input layer.

$W_{iil}$=current weight value obtained for neuron-like unit i of input layer.

G=gain factor (generally less than 1)

$X_{ios}$=actual output signal of neuron-like unit i of input layer.

$E_i = X_{ios}(1-X_{ios}) \Sigma_j E_j W_{jh1}$, (this is an error term corresponding to neuron-like unit i of input layer over all j units).

The process is iteratively repeated by entering further empirical data into the neural network and observing the output signal. If the output is in error with what the known output should be, the weights are adjusted in the manner described above. Utilizing input data known to correspond to actual physiological conditions pathologically determined, this process continues until the output is substantially consistent with such pathologically determined physiological conditions. The weights are then fixed.

Upon fixing the weights of the modulators, a solution space memory with regions indicative of normal and abnormal physiological conditions is established in the neural network. The neural network is at this stage considered trained and can make generalizations about input data by projecting input data into the solution space memory and determining which regions the input data intersects. The generalization is improved by comparing input data taken repetitively at intervals over a period of time, in the present invention taking temperature readings every five minutes over one cycle, although it is recognized that a different interval may still provide reliable results particularly when coupled with the other risk factors discussed herein as part of the present invention. The generalization relates not only to the breast as a whole but also is capable of identifying abnormal physiological conditions with a specific quadrant or other special region of the breast or breast tissue.

While the preferred embodiment has employed a multiple-layer back propagation neural network to carry out the invention, it is conceived that other means, such as myriad alternative neural network architectures or statistical programs, might be used instead of or in conjunction with the neural network. It is conceived that many variations, modifications and derivatives of the present invention are possible and the preferred embodiment set forth above is not meant to be limiting of the full scope of the invention. It is also conceived that the present invention may likewise employ other diagnostic techniques which generate information which is likewise digitzable and used to produce ROI image data for such information so that the same may be displayed in a superimposed manner to further aid the user.

The following example is presented for the purpose of illustrating the present invention, but is not intended to be limiting in the nature and scope of the present invention.

METHOD USING THERMO-PHYSIOLOGICAL VARIATIONS ASPECT OF THE INVENTION 138 subjects were recruited from the population at a surgical oncology clinics and hospitals who had been scheduled for open-breast biopsies as a result of physical exam and any mammography. Each subject wore the harness block/sensors of the present invention for a period up forty-eight hours wherein data readings were taken every five minutes.

The data were analyzed using the neural network described above which was trained using fifty-seven exemplar cases. The following results were obtained.

| | |
|---|---|
| Total biopsies: | 138 |
| Positive for cancer: | 23 |
| Cancer found by mammogram: | 19 |
| Cancer found by present invention: | 22 |
| Palpable cancers: | 17 |
| Needle localization: | 6 |

Three of the cancers detected by the present invention but not by mammography had sizes of 0.5, 0.7, and 2.0 cm in subjects aged 36, 38 and 44 respectively. In addition, the present invention indicated an additional 21 of the subjects as high risk to cancer development.

What is claimed is:

1. An apparatus for detection of precancerous and cancerous conditions in a breast, comprises:

computer based means for digitizing at least one of a mammogram image data and a (scinti)mammogram image data of a breast;

first means operably associated with the computer based means for manipulating at least one of said digitized mammogram image data and said digitized (scinti) mammogram image data and generating at least one of a mammogram ROI image and a (scinti)mammogram ROI image data indicative of precancerous and cancerous condition; and means operably associated with the computer based means for concurrently visually displaying at least one of said digitized mammogram image data and said digitized (scinti)mammogram image data and said mammogram ROI image and said (scinti)mammogram ROI image data in a superimposed manner;

means for sensing at least one of thermo-physiology of the breast and electro-physiology of the breast and generating signals in response thereto; and second means operatively associated with the sensing means for receiving and manipulating the signals and generating at least one of a thermo-physiological ROI data and an electro-physiological ROI data indicative of precancerous and cancerous conditions in the breast, wherein said displaying mean concurrently displays at least one of said digitized mammogram image data and said digitized (scinti)mammogram image data, at least one of said mammogram ROI image data and said (scinti)mammogram ROI image data and at least one of a thermo-physiological ROI data and an electro-physiological ROI data in a superimposed manner.

2. The apparatus of claim 1, wherein said computer based means includes a CPU and a scanner operably connected to said CPU.

3. The apparatus of claim 1, wherein said computer based means includes means for storing at least one of a digitized mammogram image data and digitized (scinti)mammogram image data.

4. The apparatus of claim 1, wherein said first manipulating means includes means for filtering at least one of noise, size, shape ad intensity of said digitized mammogram image data and said digitized (scinti)mammogram image data to provide a filtered data and means for regionalizing said filtered data to produce said mammogram ROI image data and said (scinti)mammogram data.

5. The apparatus of claim 1, wherein said displaying means further includes means for associating a unique visual attribute with at least one of said mammogram ROI image data, said (scinti)mammogram ROI image data, said thermo-physiological ROI data and said electro-physiological ROI data.

6. The apparatus of claim 5, wherein said attribute is a color.

7. The apparatus of claim 1, wherein said displaying means further includes means for associating a unique visual attribute with at least one of said digitized mammogram image data and said (scinti)mammogram image data and at least one of said ROI data.

8. The apparatus of claim 7, wherein said attribute is a color.

9. The apparatus of claim 1, wherein said first manipulating means includes processing means having non-algorithmic logic which utilizes prior pathological data in correspondence with said digitized data to manipulate said digitized data to produce said mammogram ROI image data and said (scinti)mammogram ROI image data.

10. The apparatus of claim 1, wherein said second manipulating means includes processing means having non-algorithmic logic which utilizes prior pathological data in correspondence with said sensed signals to manipulate said signals to produce said thermo-physiological ROI data and said electro-ROI data.

11. A method for determining and characterizing precancerous and cancerous conditions in a breast, which includes the steps of:

(a) digitizing at least one of a mammogram image data and a (scinti)mammogram image data;

(b) manipulating at least one of said digitized mammogram image data and said digitized (scinti) mammogram image data to produce at least one of a mammogram ROI image data and a (scinti) mammogram ROI image data;

(c) digitizing at least one of thermo-physiological data and an electro-physiological data of the breast;

(d) manipulating at least one of thermo-physiological ROI data and electro-physiological ROI data signals indicative of precancerous and cancerous conditions in the breast; and (e) concurrently displaying said ROI data.

12. An apparatus for detection and characterization of precancerous and cancerous conditions in a breast, which comprises:

non-invasive means adhesively connected to the breast for sensing temperature in the breast characteristic of breast cancer formation and generating temperature signals in response thereto;

first means for receiving and manipulating said signals to produce a digital output signal about said temperature signals indicative of breast cancer formation in a region of said breast, wherein said receiving and manipulating means includes a neural network having predetermined solution space memory trained on prior breast temperature signals taken over a circadian period, wherein said temperature signals are projected through said neural network to produce a generalization about said temperature signals, and wherein said generalization is used to produce said digital output signal;

second means operably for digitally producing at least one of a mammogram, image data and a (scinti) mammogram image data of a breast taken in accordance with said output signal;

third means operably associated with the second means for manipulating at least one of said digital output signal, said digitized mammogram image data and said (scinti)mammogram image data and generating at least one of a thermo-physiological ROI image data, a mammogram ROI image data and a (scinti)mammogram ROI image data indicative of precancerous and cancerous condition; and fourth means operably associated with said third means for concurrently visually displaying at least one of said digitized mammogram image data and said digitized (scinti)mammogram image data and at least one of said thermo-physiological ROI image data, said mammogram ROI image data and said (scinti)mammogram ROI image data in a superimposed manner.

13. The apparatus of claim 12, which is further characterized to include computer based device having said first means, said second means, said third means and said fourth means operably associated therewith.

14. The apparatus of claim 13, which further includes a scanner operably connected to said computer based device.

15. The apparatus of claim 13, wherein said computer based device includes means for storing at least one of a digitized mammogram image data and digitized scintimammogram image data.

16. The apparatus of claim 12, wherein said third manipulating means includes means for filtering at least one of noise, size, shape and intensity of said digitized mammogram image data and said digitized scintimammogram image data to provide a filtered data and means for regionalizing said filtered data to produce said mammogram ROI image data and said scintimammogram ROI image data.

17. The apparatus of claim 12, which further includes;
fifth means for sensing electro physiology of the breast and generating signals in response thereto;
sixth means operatively associated with the fifth means for receiving and manipulating the signals and generating an electro-physiological ROI data indicative of precancerous and cancerous conditions in the breast; and
wherein said fourth means concurrently displays said digitized mammogram image data and said digitized scintimammogram image data, at least one of said mammogram ROI image data, said scintimammogram ROI image data, said thermo-physiological ROI data and said electro-physiological ROI data in a superimposed manner.

18. The apparatus of claim 17, wherein said displaying means further includes means for associating a unique visual attribute with at least one of said mammogram ROI image data, said scintimammogram ROI image data, said thermo-physiological ROI data and said electro-physiological ROI data.

19. The apparatus of claim 18, wherein said attribute is a color.

20. The apparatus of claim 12, wherein said displaying means further includes means for associating a unique visual attribute with at least one of said mammogram ROI image data, said scintimammogram ROI image data, and said thermo-physiological ROI data.

21. The apparatus of claim 20, wherein said attribute is a color.

22. The apparatus of claim 12, wherein said first manipulating means includes processing means having non-algorithmic logic which utilizes prior pathological data in correspondence with said digitized data to manipulate said digitized data to produce said mammogram ROI image data and said scintimammogram ROI image data.

23. A method for determining and characterizing precancerous and cancerous conditions in a breast, which includes the steps of:
(a) directly sensing temperature of areas of a breast which have been predetermined highly susceptible to cancer development and generating temperature signals over a predetermined period;
(b) manipulating said temperature signals through a neural network trained on prior breast temperature signals taken over said predetermined period to produce a first digitized output signal indicative of cancerous and precancerous conditions in said area of the breast, wherein said neural network includes a predetermined solution space memory indicative of precancerous and cancerous breast tissue and breast cancer;
(c) digitizing at least one of a mammogram image data and a (scinti)mammogram image data;
(d) manipulating at least one of said first digitized output, said digitized mammogram data and said (scinti) mammogram image data and a (scinti)mammogram ROI image data; and
(e) concurrently displaying at least two of said ROI data.

24. The method of claim 23, which further includes the steps of (f) directly sensing electro-physiology of the of areas of a breast which have been predetermined highly susceptible to cancer development and (g) manipulating said temperature signals through a neural network trained on prior breast temperature signals taken over said predetermined period to produce a second digitized output signal indicative of cancerous and precancerous conditions in said area of the breast, wherein said neural network includes a predetermined solution space memory indicative of precancerous breast tissue and breast cancer; and wherein the step (d) is characterized as manipulating at least one of said first digitized output signal, said second digitized output signal, said digitized mammogram data and said scintimammogram image data to produce at least one of a thermo-physiological ROI image data, electro-physiological ROI image data a mammogram ROI image data and a scintimammogram ROI image data.

* * * * *